US012673999B2

(12) United States Patent
Vallribera et al.

(10) Patent No.: US 12,673,999 B2
(45) Date of Patent: Jul. 7, 2026

(54) ANTI-CSF-IR ANTIBODY

(71) Applicant: Roche Diagnostics Operations, Inc., Indianapolis, IN (US)

(72) Inventors: David Casagolda Vallribera, Penzberg (DE); Michael Gerg, Penzberg (DE); Michael Schraeml, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1128 days.

(21) Appl. No.: 17/704,706

(22) Filed: Mar. 25, 2022

(65) Prior Publication Data

US 2022/0235139 A1      Jul. 28, 2022

Related U.S. Application Data

(63) Continuation of application No. PCT/EP2020/076850, filed on Sep. 25, 2020.

(30) Foreign Application Priority Data

Sep. 26, 2019      (EP) ..................................... 19199834

(51) Int. Cl.
*C07K 16/28*      (2006.01)
*G01N 33/575*      (2026.01)
(52) U.S. Cl.
CPC ..... *C07K 16/2866* (2013.01); *G01N 33/5759* (2026.01); *C07K 2317/40* (2013.01); *C07K 2317/565* (2013.01)
(58) Field of Classification Search
CPC .......... C07K 2317/565; C07K 2317/56; C07K 14/7153; C07K 16/243; A61K 2039/505; G01N 2333/7153
See application file for complete search history.

(56) References Cited

U.S. PATENT DOCUMENTS

2017/0355756 A1* 12/2017 Julien .................... C07K 16/18

FOREIGN PATENT DOCUMENTS

| WO | WO-2008068048 A2 * | 6/2008 | .............. A61P 31/10 |
|----|------|--------|-------|
| WO | 2009026303 A1 | 2/2009 | |
| WO | 2009112245 A1 | 3/2009 | |
| WO | WO-2009033743 A1 * | 3/2009 | .............. A61P 25/28 |
| WO | 2011070024 A1 | 6/2011 | |
| WO | 2011123381 A1 | 10/2011 | |
| WO | 2011140249 A2 | 11/2011 | |
| WO | 2012150320 A1 | 5/2012 | |
| WO | 2012110360 A1 | 8/2012 | |
| WO | 2015044083 A1 | 9/2014 | |
| WO | WO-2019069993 A1 * | 4/2019 | .............. A61P 37/00 |

OTHER PUBLICATIONS

Al Qaraghuli et al. (2020, Nature Scientific Reports 10:13969) (Year: 2020).*
Rabia, et al. (2018, Biochemical Engineering Journal 137:365-374) (Year: 2018).*
Tiller et al (2017, J. Biol. Chem. (2017) 292(40) 16638-16652) (Year: 2017).*
Tsuji et al (2022, J Virol 96:e00071-22) (Year: 2022).*
International Search Report, European Patent Office, International Patent Application No. PCT/EP2020/076850, Feb. 12, 2021, 6 pages.
Written Opinion of the International Searching Authority, European Patent Office, International Patent Application No. PCT/EP2020/076850, Feb. 12, 2021, 5 pages.
International Preliminary Report on Patentability, European Patent Office, International Patent Application No. PCT/EP2020/076850, Mar. 15, 2022, 6 pages.
Needleman et al., A General Method Applicable to the Search for Similarities in the Amino Acid Sequence of Two Proteins, J. Mol. Biol., vol. 48, 1970, pp. 444-453.
Pearson et al., Improved tools for biological sequence comparison, Proc. Natl. Acad. Sci. (USA), vol. 85, 1988, pp. 2444.
Kuby, J.: "Immunology", 1997, W.H. Freeman & CO.
Cannarile et al., Colony-stimulating factor 1 receptor (CSF1R) inhibitors in cancer therapy, Journal for Immunotherapy of Cancer, vol. 5, No. 1, 2017, pp. 53.
Seeber et al., A Robust High Throughput Platform to Generate FunctionalRecombinant Monoclonal Antibodies Using Rabbit B Cellsfrom Peripheral Blood, PLOS ONE, vol. 9, No. 2, Feb. 4, 2014.
Anonymous, Phospho-M-CSF Receptor (Tyr708) (D5F4Y) Rabbit mAb, Nov. 1, 2014.
Anonymous, Phospho-M-CSF Receptor (Tyr723) (49C10) Rabbit mAb, Apr. 20, 2017.
Anonymous, M-CSF Receptor (E4T8Z) Rabbit mAb, Nov. 1, 2018.
Cannarile, M. A., et al. (2017), J Immunother Cancer 5(1): 53.
Coussens, L., et al., Nature 320 (1986) 277-280.
Downing et al., Molecular and Cellular Biology, vol. 11, No. 5, May 1, 1991, pp. 2489-2495.
El-Gamal et al., J Med Chem. 2018, 61(13):5450-5466.
Flick et al., Oncogene, vol. 14, No. 21, May 1, 1997, pp. 2553-2561.
Hume et al., Blood 119 (2012) 1810-1820.
Needleman and Wunsch J. Mol. Biol. 48:443 (1970), by the search for similarity method of Pearson and Lipman Proc. Natl. Acad. Sci. (USA) 85: 2444 (1988).
Pixley et al., Trends Cell Biol. 14 (2004) 628-638.

(Continued)

*Primary Examiner* — Gregory S Emch
*Assistant Examiner* — Ashley H. Gao
(74) *Attorney, Agent, or Firm* — Taft Stettinius & Hollister LLP

(57) ABSTRACT

The present invention relates to a monoclonal antibody, or fragment thereof, which binds to CSF-1R (Colony stimulating factor 1 receptor), in particular to human CSF-1R. The present invention further relates to the in vitro use of the monoclonal antibody, or fragment thereof, of the present invention for the detection of CSF-1R in a sample. Further encompassed by the present invention is a complex comprising the monoclonal antibody, or fragment thereof, of the present invention and CSF-1R such as the human CSF-1R polypeptide.

14 Claims, 5 Drawing Sheets

Figures 1, 2:
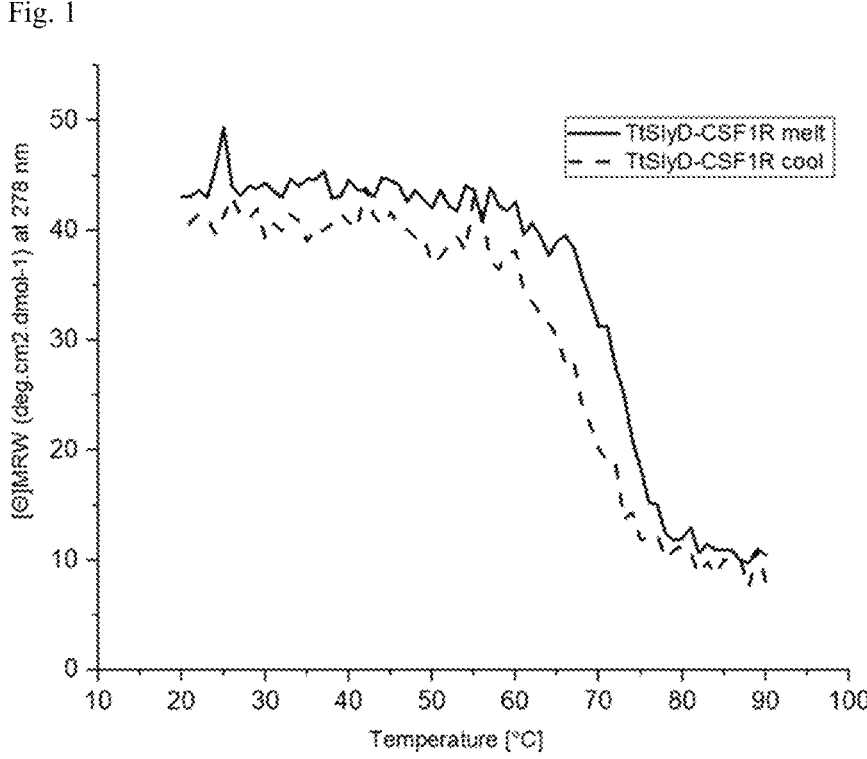

Specification includes a Sequence Listing.

(56) References Cited

OTHER PUBLICATIONS

Rice, P., Longden, I., and Bleasby, A., The European Molecular Biology Open Software Suite, Trends in Genetics 16 (6), 276-277, 2000.

Ries, C. H., et al. (2014), Cancer Cell 25(6): 846-859.

Roussel, M.F., et al., Nature 325 (1987) 549-552.

Roth, P., and Stanley, E.R., Curr. Top. Microbiol. Immunol. 181 (1992) 141-167).

Smith and Waterman Add. APL. Math. 2:482 (1981).

Stanley et al., Stem Cells 12 Suppl. 1 (1995) 15-24.

Stanley et al., Mol. Reprod. Dev. 46 (1997) 4-10.

Wang et al., Molecular and Cellular Biology 13 (1993) 5348-5359.

Xiong, Y. et al., J. Biol. Chem. 286 (2011) 952-960.

Yu et al., Journal of Biological Chemistry, vol. 287, No. 17, Apr. 20, 2012, pp. 13694-13704.

Achkova and Maher, Biochem. Soc. Trans., 2016, vol. 44, No. 2, pp. 333-341.

* cited by examiner

Peptide Sequence
SEQ ID NO 13 to 21

% Signal

SEQ ID NO: 13: P-E-G-G-V-D-pY-K-N-I-H-L-E-K-K,    100.0
SEQ ID NO: 14: E-G-G-V-D-pY-K-N-I-H-L-E-K-K-pY    55.3
SEQ ID NO 15: G-G-V-D-pY-K-N-I-H-L-E-K-K-pY-V    57.1
SEQ ID NO 16: G-V-D-pY-K-N-I-H-L-E-K-K-pY-V-R    73.3
SEQ ID NO 17: V-D-pY-K-N-I-H-L-E-K-K-pY-V-R-R    91.8
SEQ ID NO 18: D-pY-K-N-I-H-L-E-K-K-pY-V-R-R-D    49.8
SEQ ID NO 19: pY-K-N-I-H-L-E-K-K-pY-V-R-R-D-S    62.6
SEQ ID NO 20: K-N-I-H-L-E-K-K-pY-V-R-R-D-S-G    48.9
SEQ ID NO 21: N-I-H-L-E-K-K-pY-V-R-R-D-S-G-F    45.7

SEQUENCE LISTING

```
<160> NUMBER OF SEQ ID NOS: 21

<210> SEQ ID NO 1
<211> LENGTH: 10
<212> TYPE: PRT
<213> ORGANISM: Homo sapiens

<400> SEQUENCE: 1

Tyr Lys Asn Ile His Leu Glu Lys Lys Tyr
1               5                   10

<210> SEQ ID NO 2
<211> LENGTH: 110
<212> TYPE: PRT
<213> ORGANISM: Artificial Sequence
<220> FEATURE:
<223> OTHER INFORMATION: light chain variable domain

<400> SEQUENCE: 2

Ala Ala Val Leu Thr Gln Thr Pro Ser Pro Val Ser Ala Ala Val Gly
1               5                   10                  15

Gly Thr Val Thr Ile Ser Cys Gln Ser Ser Glu Ser Val Tyr Ser Asn
                20                  25                  30

Asn Phe Leu Ser Trp Tyr Gln Leu Lys Pro Gly Gln Arg Pro Arg Leu
            35                  40                  45

Leu Ile Tyr Glu Ala Ser Lys Val Ala Ser Gly Val Pro Ser Arg Phe
        50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ala Gly Gly Tyr Asp Val
                85                  90                  95

Ser Asp Asp Ala Phe Gly Gly Gly Thr Glu Val Leu Val Lys
            100                 105                 110

<210> SEQ ID NO 3
<211> LENGTH: 114
<212> TYPE: PRT
<213> ORGANISM: Artificial Sequence
<220> FEATURE:
<223> OTHER INFORMATION: heavy chain variable domain

<400> SEQUENCE: 3

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Arg Tyr Trp
                20                  25                  30

Met Thr Trp Val Arg Gln Ala Pro Gly Lys Gly Leu Glu Tyr Ile Gly
            35                  40                  45

Trp Ile Asp Arg Ser Gly Asn Thr Tyr Phe Ala Asp Trp Ala Lys Gly
        50                  55                  60

Arg Phe Thr Gly Ser Lys Thr Ser Thr Thr Arg Asp Leu Lys Ile Thr
```

```
65                    70                    75                    80
Ser Pro Thr Thr Glu Asp Thr Ala Thr Tyr Phe Cys Gly Arg Gly Gly
                   85                    90                    95
Gln Asn Asn Gly Tyr Asp Leu Trp Gly Pro Gly Thr Leu Val Thr Val
             100                  105                  110
Ser Ser

<210> SEQ ID NO 4
<211> LENGTH: 13
<212> TYPE: PRT
<213> ORGANISM: Artificial Sequence
<220> FEATURE:
<223> OTHER INFORMATION: light chain CDR1

<400> SEQUENCE: 4

Gln Ser Ser Glu Ser Val Tyr Ser Asn Asn Phe Leu Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: light chain CDR2

<400> SEQUENCE: 5

Glu Ala Ser Lys Val Ala Ser
1               5

<210> SEQ ID NO 6
<211> LENGTH: 10
<212> TYPE: PRT
<213> ORGANISM: Artificial Sequence
<220> FEATURE:
<223> OTHER INFORMATION: light chain CDR3

<400> SEQUENCE: 6

Ala Gly Gly Tyr Asp Val Ser Asp Asp Ala
1               5                   10

<210> SEQ ID NO 7
<211> LENGTH: 13
<212> TYPE: PRT
<213> ORGANISM: Artificial Sequence
<220> FEATURE:
<223> OTHER INFORMATION: heavy chain CDR1

<400> SEQUENCE: 7

Thr Ala Ser Gly Phe Ser Leu Ser Arg Tyr Trp Met Thr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: heavy chain CDR2

<400> SEQUENCE: 8

Arg Ser Gly Asn Thr Tyr Phe Ala Asp Trp Ala Lys Gly
1               5                   10

<210> SEQ ID NO 9
<211> LENGTH: 9
<212> TYPE: PRT
```

```
<213> ORGANISM: Artificial Sequence
<220> FEATURE:
<223> OTHER INFORMATION: heavy chain CDR3

<400> SEQUENCE: 9

Gly Gly Gln Asn Asn Gly Tyr Asp Leu
1               5

<210> SEQ ID NO 10
<211> LENGTH: 971
<212> TYPE: PRT
<213> ORGANISM: Homo sapiens

<400> SEQUENCE: 10

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
        50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
        130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
        210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Leu Asn Leu Ser
        290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335
```

```
Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
            370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
            435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Val Ala Cys Met Ser Ile Met Ala Leu
            515                 520                 525

Leu Leu Leu Leu Leu Leu Leu Leu Leu Tyr Lys Tyr Lys Gln Lys Pro
            530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
            610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
            675                 680                 685

Pro Gly Gln Asp Pro Glu Gly Gly Val Asp Tyr Lys Asn Ile His Leu
            690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750
```

-continued

```
Arg Asp Leu Leu His Phe Ser Ser Gln Val Ala Gln Gly Met Ala Phe
        755             760             765
```

```
Leu Ala Ser Lys Asn Cys Ile His Arg Asp Val Ala Ala Arg Asn Val
        770             775             780
```

```
Leu Leu Thr Asn Gly His Val Ala Lys Ile Gly Asp Phe Gly Leu Ala
785             790             795             800
```

```
Arg Asp Ile Met Asn Asp Ser Asn Tyr Ile Val Lys Gly Asn Ala Arg
            805             810             815
```

```
Leu Pro Val Lys Trp Met Ala Pro Glu Ser Ile Phe Asp Cys Val Tyr
        820             825             830
```

```
Thr Val Gln Ser Asp Val Trp Ser Tyr Gly Ile Leu Leu Trp Glu Ile
        835             840             845
```

```
Phe Ser Leu Gly Leu Asn Pro Tyr Pro Gly Ile Leu Val Asn Ser Lys
        850             855             860
```

```
Phe Tyr Lys Leu Val Lys Asp Gly Tyr Gln Met Ala Gln Pro Ala Phe
865             870             875             880
```

```
Ala Pro Lys Asn Ile Tyr Ser Ile Met Gln Ala Cys Trp Ala Leu Glu
            885             890             895
```

```
Pro Thr His Arg Pro Thr Phe Gln Gln Ile Cys Ser Phe Leu Gln Glu
            900             905             910
```

```
Gln Ala Gln Glu Asp Arg Arg Glu Arg Asp Tyr Thr Asn Leu Pro Ser
        915             920             925
```

```
Ser Ser Arg Ser Gly Gly Ser Gly Ser Ser Ser Glu Leu Glu Glu
        930             935             940
```

```
Glu Ser Ser Ser His Leu Thr Cys Cys Glu Gln Gly Asp Ile Ala Gln
945             950             955             960
```

```
Pro Leu Leu Gln Pro Asn Asn Tyr Gln Phe Cys
                965             970
```

```
<210> SEQ ID NO 11
<211> LENGTH: 193
<212> TYPE: PRT
<213> ORGANISM: Artificial Sequence
<220> FEATURE:
<223> OTHER INFORMATION: TtSlyD-CSF1R

<400> SEQUENCE: 11
```

```
Met Arg Ser Lys Val Gly Gln Asp Lys Val Val Thr Ile Arg Tyr Thr
1               5               10              15
```

```
Leu Gln Val Glu Gly Glu Val Leu Asp Gln Gly Glu Leu Ser Tyr Leu
            20              25              30
```

```
His Gly His Arg Asn Leu Ile Pro Gly Leu Glu Glu Ala Leu Glu Gly
        35              40              45
```

```
Arg Glu Glu Gly Glu Ala Phe Gln Ala His Val Pro Ala Glu Lys Ala
        50              55              60
```

```
Tyr Gly Ala Gly Ser Met Leu Gly Pro Ser Leu Ser Pro Gly Gln Asp
65              70              75              80
```

```
Pro Glu Gly Gly Val Asp Tyr Lys Asn Ile His Leu Glu Lys Lys Tyr
            85              90              95
```

```
Val Arg Arg Asp Ser Gly Phe Ser Ser Gln Gly Val Asp Thr Tyr Val
            100             105             110
```

```
Glu Met Arg Pro Val Ser Thr Ser Ser Asn Asp Ser Phe Ser Glu Gln
        115             120             125
```

```
Asp Leu Asp Lys Glu Asp Gly Arg Pro Gly Ser Ser Gly Lys Asp Leu
        130             135             140
```

Asp Phe Gln Val Glu Val Val Lys Val Arg Glu Ala Thr Pro Glu Glu
145             150             155             160

Leu Leu His Gly His Ala His Gly Gly Gly Ser Arg Pro Leu Leu Pro
                165             170             175

Pro Leu Pro Gly Gly Gly Ser Arg Lys His His His His His His His
            180             185             190

His

<210> SEQ ID NO 12
<211> LENGTH: 125
<212> TYPE: PRT
<213> ORGANISM: Artificial Sequence
<220> FEATURE:
<223> OTHER INFORMATION: TtSlyDsh3

<400> SEQUENCE: 12

Met Arg Ser Lys Val Gly Gln Asp Lys Val Val Thr Ile Arg Tyr Thr
1               5               10              15

Leu Gln Val Glu Gly Glu Val Leu Asp Gln Gly Glu Leu Ser Tyr Leu
            20              25              30

His Gly His Arg Asn Leu Ile Pro Gly Leu Glu Glu Ala Leu Glu Gly
        35              40              45

Arg Glu Glu Gly Glu Ala Phe Gln Ala His Val Pro Ala Glu Lys Ala
    50              55              60

Tyr Gly Ala Gly Ser Gly Ser Ser Gly Lys Asp Leu Asp Phe Gln Val
65              70              75              80

Glu Val Val Lys Val Arg Glu Ala Thr Pro Glu Glu Leu Leu His Gly
            85              90              95

His Ala His Gly Gly Gly Ser Arg Pro Leu Leu Pro Pro Leu Pro Gly
            100             105             110

Gly Gly Ser Arg Lys His His His His His His His
        115             120             125

<210> SEQ ID NO 13
<211> LENGTH: 15
<212> TYPE: PRT
<213> ORGANISM: Artificial Sequence
<220> FEATURE:
<223> OTHER INFORMATION: Epitope
<220> FEATURE:
<221> NAME/KEY: MOD_RES
<222> LOCATION: (7)..(7)
<223> OTHER INFORMATION: PHOSPHORYLATION

<400> SEQUENCE: 13

Pro Glu Gly Gly Val Asp Tyr Lys Asn Ile His Leu Glu Lys Lys
1               5               10              15

<210> SEQ ID NO 14
<211> LENGTH: 15
<212> TYPE: PRT
<213> ORGANISM: Artificial Sequence
<220> FEATURE:
<223> OTHER INFORMATION: Epitope
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION

<400> SEQUENCE: 14

-continued

```
Glu Gly Gly Val Asp Tyr Lys Asn Ile His Leu Glu Lys Lys Tyr
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Epitope
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 15

Gly Gly Val Asp Tyr Lys Asn Ile His Leu Glu Lys Lys Tyr Val
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Epitope
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 16

Gly Val Asp Tyr Lys Asn Ile His Leu Glu Lys Lys Tyr Val Arg
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Epitope
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 17

Val Asp Tyr Lys Asn Ile His Leu Glu Lys Lys Tyr Val Arg Arg
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Epitope
<220> FEATURE:
<221> NAME/KEY: MOD_RES
<222> LOCATION: (2)..(2)
<223> OTHER INFORMATION: PHOSPHORYLATION
<220> FEATURE:
```

-continued

```
<221> NAME/KEY: MOD_RES
<222> LOCATION: (11)..(11)
<223> OTHER INFORMATION: PHOSPHORYLATION

<400> SEQUENCE: 18

Asp Tyr Lys Asn Ile His Leu Glu Lys Lys Tyr Val Arg Arg Asp
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Epitope
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 19

Tyr Lys Asn Ile His Leu Glu Lys Lys Tyr Val Arg Arg Asp Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Epitope
<220> FEATURE:
<221> NAME/KEY: MOD_RES
<222> LOCATION: (9)..(9)
<223> OTHER INFORMATION: PHOSPHORYLATION

<400> SEQUENCE: 20

Lys Asn Ile His Leu Glu Lys Lys Tyr Val Arg Arg Asp Ser Gly
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Epitope
<220> FEATURE:
<221> NAME/KEY: MOD_RES
<222> LOCATION: (8)..(8)
<223> OTHER INFORMATION: PHOSPHORYLATION

<400> SEQUENCE: 21

Asn Ile His Leu Glu Lys Lys Tyr Val Arg Arg Asp Ser Gly Phe
1               5                   10                  15
```

ANTI-CSF-IR ANTIBODY

CROSS-REFERENCE TO RELATED APPLICATIONS

This application is a continuation of International Application No. PCT/EP2020/076850 filed Sep. 25, 2020, which claims priority to European Application 19199834.3 filed Sep. 26, 2019, the disclosures of which are hereby incorporated by reference in their entirety.

INCORPORATION OF SEQUENCE LISTING

A paper copy of the Sequence Listing and a computer readable form of the Sequence Listing containing the file named "P34782-US Sequence Listing ST25", which is 1,546 bytes in size (as measured in MICROSOFT WINDOWS® EXPLORER), are provided herein and are herein incorporated by reference. This Sequence Listing consists of SEQ ID NOs: 1-21.

FIELD OF THE INVENTION

The present invention relates to a monoclonal antibody, or fragment thereof, which binds to CSF-1R (Colony stimulating factor 1 receptor), in particular to human CSF-1R. The present invention further relates to the in vitro use of the monoclonal antibody, or fragment thereof, of the present invention for the detection of CSF-1R in a sample. Further encompassed by the present invention is a complex comprising the monoclonal antibody, or fragment thereof, of the present invention and CSF-1R such as the human CSF-1R polypeptide.

BACKGROUND OF THE INVENTION

The human CSF-1 receptor (CSF-1R; colony stimulating factor 1 receptor) is a growth factor and encoded by the c-fms proto-oncogene (reviewed e.g. in Roth, P., and Stanley, E. R., Curr. Top. Microbiol. Immunol. 181 (1992) 141-167).

Currently two CSF-1R ligands that bind to the extracellular domain of CSF-1R are known. The first one is CSF-1 (colony stimulating factor 1) and is found extracellularly as a disulfide-linked homodimer (Stanley et al., Stem Cells 12 Suppl. 1 (1995) 15-24). The second one is IL-34 (Hume et al., Blood 119 (2012) 1810-1820). The main biological effects of CSF-1R signaling are the differentiation, proliferation, migration, and survival of hematopoietic precursor cells to the macrophage lineage. Activation of CSF-1R is mediated by its CSF-1R ligands, CSF-1 and IL-34. Binding of CSF-1 to CSF-1R induces the formation of homodimers and activation of the kinase by tyrosine phosphorylation (Stanley et al., Mol. Reprod. Dev. 46 (1997) 4-10).

CSF-1R has been associated with many diseases and disorders (see e.g. Cannarile, M. A., et al. (2017), J Immunother Cancer 5(1): 53, Ries, C. H., et al. (2014), Cancer Cell 25(6): 846-859). For example, CSF-1R plays an important role in initiating inflammatory, cancer, and bone disorders. Therefore, many CSF-1R inhibitors (such as small molecule inhibitors and monoclonal antibodies) have been described and are analyzed in clinical trials (reviewed by El-Gamal et al., J Med Chem. 2018, 61(13):5450-5466).

Anti-CSF-1R antibodies are e.g. disclosed in WO2011/123381, WO2011/140249 and WO2012/110360.

The extracellular domain of the CSF-1 receptor (CSF-1R-ECD) comprises five subdomains (D1 to D5). The biologically active homodimer CSF-1 binds to the CSF-1R within the subdomains D1 to D3. The subdomains D4 to D5 of the extracellular domain are not involved in the CSF-1 binding (Wang et al., Molecular and Cellular Biology 13 (1993) 5348-5359). The subdomain D4 is involved in dimerization (Pixley et al., Trends Cell Biol. 14 (2004) 628-638).

Many therapeutic candidate anti-CSF-1R antibodies bind to the extracellular domain of the CSF-1 receptor (CSF-1R-ECD). E.g. WO 2009/026303 and WO 2009/112245 disclose anti-CSF-1R antibodies binding to CSF-1R within the first three subdomains (D1 to D3) of the extracellular domain. WO2011/070024 discloses anti-CSF-1R antibodies binding to CSF-1R within the dimerization domain (D4 to D5).

In addition to antibodies which bind to the extracellular domain of the CSF-1 receptor, antibodies which bind to other domains have been described such as antibodies which bind the CSF-1R kinase domain. For example, polyclonal antibodies which bind to phosphorylation sites of CSF-1R are commercially available from Thermo Fisher such as Phospho-CSF1R (Tyr561), Phospho-CSF1R (Tyr699), Phospho-CSF1R (Tyr708), Phospho-CSF1R (Tyr723), Phospho-CSF1R (Tyr809), Phospho-CSF1R (Tyr921). The polyclonal antibodies were generated by using chemically synthesized phosphopeptides as immunogen.

Further, a monoclonal antibody has been produced by immunizing rabbits with a synthetic phosphopeptide corresponding to residues surrounding Tyr708 of human CSF-1R receptor protein. The antibody, termed "Phospho-M-CSF Receptor (Tyr708) (D5F4Y) Rabbit mAb #14591" is commercially available from Bioke (Leiden, The Netherlands). The antibody recognizes endogenous levels of CSF-1R only when phosphorylated at Tyr708, but may cross-react with other activated protein tyrosine kinases such as phospho-Src. Accordingly, the antibody might not be suitable for immunohistochemistry (IHC).

WO2012/150320 describes a scaffold technology for the production of antibodies. The document describes a fusion polypeptide comprising one or more fragments of a peptidyl-prolyl cis/trans isomerase or FKBP domain family members and its use in methods for antibody screening/selection, for epitope mapping as well as its use as immunogen for the production of antibodies specifically binding an immunogenic peptide or secondary structure presented by the fusion polypeptide. WO2015/044083 discloses that the *Thermus thermophilus* SlyD FKBP domain is suited in the fusion polypeptide for generating antibodies.

The inventors have grafted a fragment of the kinase domain of human CSF-1R onto the *Thermus thermophilus* SlyD FKBP scaffold. The generated fusion polypeptide was used as immunogen for the generation of monoclonal antibodies in rabbits. It was shown that the antibodies showed high antibody/receptor affinity and specificity versus CSF-1R, in particular the antibody termed "1H11". The antibody showed excellent immunohistochemistry performance and could be therefore applied in clinical studies with small molecules or antibodies targeting CSF-1R. Surprisingly, the antibody was capable of detecting both native and denatured CSF-1R.

BRIEF SUMMARY OF THE PRESENT INVENTION

The present invention relates to a monoclonal antibody, or fragment thereof, which binds to CSF-1R (Colony stimulating factor 1 receptor), in particular to human CSF-1R.

In an embodiment of the present invention, the monoclonal antibody, or fragment thereof, comprises a light chain variable domain that is at least 85% identical to the light chain variable domain having a sequence as shown in SEQ ID NO: 2, and/or wherein said monoclonal antibody, or fragment thereof, comprises a heavy chain variable domain that is at least 85% identical to the heavy chain variable domain having a sequence as shown in SEQ ID NO: 3.

In an embodiment of the present invention, the monoclonal antibody, or fragment thereof, comprises (a) a light chain variable domain comprising
    (a1) a light chain CDR1 that differs by not more than a total of three amino acid additions, substitutions, and/or deletions from a light chain CDR1 having an amino acid sequence as shown in SEQ ID NO: 4 (QSSESVYSNNFLS),
    (a2) a light chain CDR2 that differs by not more than a total of three amino acid additions, substitutions, and/or deletions from a light chain CDR2 having an amino acid sequence as shown in SEQ ID NO: 5 (EASKVAS), and/or
    (a3) a light chain CDR3 that differs by not more than a total of three amino acid additions, substitutions, and/or deletions from a light chain CDR3 having an amino acid sequence as shown in SEQ ID NO: 6 (AGGYDVSDDA), (b) a heavy chain variable domain comprising
    (b1) a heavy chain CDR1 that differs by not more than a total of three amino acid additions, substitutions, and/or deletions from a heavy chain CDR1 having an amino acid sequence as shown in SEQ ID NO: 7 (TASGFSLSRYWMT),
    (b2) a heavy chain CDR2 that differs by not more than a total of three amino acid additions, substitutions, and/or deletions from a heavy chain CDR2 having an amino acid sequence as shown in SEQ ID NO: 8 (RSGNTYFADWAKG), and/or
    (b3) a heavy chain CDR3 that differs by not more than a total of three amino acid additions, substitutions, and/or deletions from a heavy chain CDR3 having an amino acid sequence as shown in SEQ ID NO: 9 (GGQNNGYDL), or (c) both the light chain variable domain as defined under (a) and the heavy chain variable domain as defined under (b).

In an embodiment of the monoclonal antibody of the present invention, or the fragment thereof, the epitope of the monoclonal antibody, or fragment thereof, comprises a sequence as shown in SEQ ID NO: 1 (YKNIHLEKKY). Preferably, at least one of the two Tyrosine residues, in particular both Tyrosine residues, of said epitope is phosphorylated.

In an embodiment, the monoclonal antibody, or fragment thereof, comprises (a) a light chain variable domain comprising
    (a1) a light chain CDR1 having a sequence as shown in SEQ ID NO: 4 (QSSESVYSNNFLS),
    (a2) a light chain CDR2 having a sequence as shown in SEQ ID NO: 5 (EASKVAS), and
    (a3) a light chain CDR3 having a sequence as shown in SEQ ID NO: 6 (AGGYDVSDDA), and (b) a heavy chain variable domain comprising
    (b1) a heavy chain CDR1 having a sequence as shown in SEQ ID NO: 7 (TASGFSLSRYWMT),
    (b2) a heavy chain CDR2 having a sequence as shown in SEQ ID NO: 8 (RSGNTYFADWAKG), and (b3) a heavy chain CDR3 having a sequence as shown in SEQ ID NO: 9 (GGQNNGYDL).

The present invention further relates to the in vitro use of the monoclonal antibody, or fragment thereof, of any one the present invention for the detection of CSF-1R in a sample.

The present invention further contemplates a method for detecting CSF-1R in a sample, comprising (a) contacting a sample comprising CSF-1R with the monoclonal antibody, or fragment thereof, of the present invention, thereby forming a complex comprising CSF-1R and said monoclonal antibody, or fragment thereof, and (b) detecting the complex formed in step (a), thereby detecting CSF-1R in said sample.

The present invention further contemplates a complex comprising the monoclonal antibody, or fragment thereof, of the present invention and CSF-1R such as the human CSF-1R polypeptide.

DETAILED DESCRIPTION OF THE INVENTION

As set forth above, the present invention relates to a monoclonal antibody, or fragment thereof, which binds to CSF-1R (Colony stimulating factor 1 receptor), in particular to human CSF-1R.

CSF-1R is a polypeptide belonging to the class III subfamily of receptor tyrosine kinases and is encoded by the c-fms proto-oncogene. Synonyms of CSF-1R are M-CSF receptor; Macrophage colony-stimulating factor 1 receptor, Fms proto-oncogene and c-fms. Binding of CSF-1 or IL-34 induces receptor dimerization, followed by autophosphorylation and activation of downstream signaling cascades. Activation of CSF-IR regulates the survival, proliferation and differentiation of monocytes and macrophages (Xiong, Y. et al., J. Biol. Chem. 286 (2011) 952-960). Preferably, the monoclonal antibody (or antigen-binding fragment thereof) of the present invention binds to the human CSF-1R polypeptide. Human CSF-IR is known since 1986 (Coussens, L., et al, Nature 320 (1986) 277-280). The cloning of the receptor was described for the first time in Roussel, M. F., et al., Nature 325 (1987) 549-552. CSF-1R is a single chain, transmembrane receptor tyrosine kinase (RTK) and a member of the family of immunoglobulin (Ig) motif containing RTKs characterized by 5 repeated Ig-like subdomains D1-D5 in the extracellular domain (ECD) of the receptor (Wang, Z., et al Molecular and Cellular Biology 13 (1993) 5348-5359). The intracellular domain of CSF-1R comprises, inter alia, the kinase domain of CSF-1R.

The amino acid sequence of full length human CSF-1R is as follows (SEQ ID NO: 10):
MGPGVLLLLLVATAWHGQGIPVIEPSVPELVVKPGATVTLRCVGNGSVEW

DGPPSPHWTLYSDGSSILSTNNATFQNTGTYRCTEPGDPLGGSAAIHLY

VKDPARPWNVLAQEVVVFEDQDALLPCLLTDPVLEAGVSLVRVRGRPLMR

HTNYSFSPWHGFTIHRAKFIQSQDYQCSALMGGRKVMSISIRLKVQKVIP

GPPALTLVPAELVRIRGEAAQIVCSASSVDVNFDVFLQHNNTKLAIPQQS

DFHNNRYQKVLTLNLDQVDFQHAGNYSCVASNVQGKHSTSMFFRVVESAY

LNLSSEQNLIQEVTVGEGLNLKVMVEAYPGLQGFNWTYLGPFSDHQPEPK

LANATTKDTYRHTFTLSLPRLKPSEAGRYSFLARNPGGWRALTFELTLRY

-continued

```
PPEVSVIWTFINGSGTLLCAASGYPQPNVTWLQCSGHTDRCDEAQVLQVW

DDPYPEVLSQEPFHKVIVQSLLTVETLEHNQTYECRAHNSVGSGSWAFIP

ISAGAHTHPPDEFLFTPVVVACMSIMALLLLLLLLLLLYKYKQKPKYQVRW

KIIESYEGNSYTFIDPTQLPYNEKWEFPRNNLQFGKTLGAGAFGKVVEAT

AFGLGKEDAVLKVAVKMLKSTAHADEKEALMSELKIMSHLGQHENIVNL

LGACTHGGPVLVITEYCCYGDLLNFLRRKAEAMLGPSLSPGQDPEGGVD

YKNIHLEKKY
VRRDSGFSSQGVDTYVEMRPVSTSSNDSFSEQDLDKEDGR

PLELRDLLHFSSQVAQGMAFLASKNCIHRDVAARNVLLTNGHVAKIGDF

GLARDIMNDSNYIVKGNARLPVKWMAPESIFDCVYTVQSDVWSYGILLWE

IFSLGLNPYPGILVNSKFYKLVKDGYQMAQPAFAPKNIYSIMQACWALEP

THRPTFQQICSFLQEQAQEDRRERDYTNLPSSSRSGGSGSSSSELEEESS

SHLTCCEQGDIAQPLLQPNNYQFC
```

The extracellular domain of human CSF-1R is underlined, the intracellular domain is shown in italics in the above sequence. The first 19 amino acids (signal peptide) are cleaved off after translation to form the mature form of the CSF-1R polypeptide. The epitope region of the antibody identified in studies underlying the present invention is shown in bold. The sequence of the epitope is also shown in SEQ ID NO: 1 (YKNIHLEKKY). As described herein below in more detail, the Tyrosine residue at position 699 and/or the Tyrosine residue at position 708 is/are phosphorylated.

Advantageously, the antibody of the present invention binds to both the native form, i.e. the undenatured form, of CSF-1R and the denatured form of CSF-1R. Thus, the term "CSF-1R" includes native CSF-1R and denatured CSF-1.

The antibody, or antigen-binding fragment of the present invention shall have the following sequence:

Preferably, the monoclonal antibody, or fragment thereof, which binds to CSF-1R (Colony stimulating factor 1 receptor) comprises a light chain variable domain that is, in increasing order of preference at least 70%, 75%, 80%, 85%, 90%, 95%, 98%, or 99% identical to the light chain variable domain having a sequence as shown in SEQ ID NO: 2, and/or a heavy chain variable domain that is at least 70%, 75%, 80%, 85%, 90%, 95%, 98%, or 99% identical to the heavy chain variable domain having a sequence as shown in SEQ ID NO: 3. In particular, the monoclonal antibody, or fragment thereof, comprises a light chain variable domain that is, in increasing order of preference at least 70%, 75%, 80%, 85%, 90%, 95%, 98%, or 99% identical to the light chain variable domain having a sequence as shown in SEQ ID NO: 2, and a heavy chain variable domain that is at least 70%, 75%, 80%, 85%, 90%, 95%, 98%, or 99% identical to the heavy chain variable domain having a sequence as shown in SEQ ID NO: 3. For example, the monoclonal antibody, or fragment thereof, comprises a light chain variable domain that is, in increasing order of preference at least 85% identical to the light chain variable domain having a sequence as shown in SEQ ID NO: 2, and a heavy chain variable domain that is at least 85% identical to the heavy chain variable domain having a sequence as shown in SEQ ID NO: 3.

In an aspect, the monoclonal antibody comprises a light chain variable domain having a sequence as shown in SEQ ID NO: 2, and a heavy chain variable domain having a sequence as shown in SEQ ID NO: 3.

```
The sequence of the light chain variable region is
a follows (SEQ ID NO: 2):
AAVLTQTPSPVSAAVGGTVTISCQSSESVYSNNFLSWYQLKPGQRPRLLI

YEASKVASGVPSRFSGSGSGTQFTLTISGVQCDDAATYYCAGGYDVSDDA

FGGGTEVLVK

The sequence of the heavy chain variable region is
a follows (SEQ ID NO: 3):
QSVEESGGRLVTPGTPLTLTCTASGFSLSRYWMTWVRQAPGKGLEYIGWI

DRSGNTYFADWAKGRFTGSKTSTTRDLKITSPTTEDTATYFCGRGGQNNG

YDLWGPGTLVTVSS
```

Alternatively or additionally, the monoclonal antibody, or fragment thereof, of the present invention comprises (a) a light chain variable domain comprising
   (a1) a light chain CDR1 that differs by not more than a total of three, two, or in particular one amino acid additions, substitutions, and/or deletions from a light chain CDR1 having an amino acid sequence as shown in SEQ ID NO: 4 (QSSESVYSNNFLS),
   (a2) a light chain CDR2 that differs by not more than a total of three, two, or in particular one amino acid additions, substitutions, and/or deletions from a light chain CDR2 having an amino acid sequence as shown in SEQ ID NO: 5 (EASKVAS), and/or
   (a3) a light chain CDR3 that differs by not more than a total of three, two, or in particular one amino acid additions, substitutions, and/or deletions from a light chain CDR3 having an amino acid sequence as shown in SEQ ID NO: 6 (AGGYDVSDDA), and/or
(b) a heavy chain variable domain comprising
   (b1) a heavy chain CDR1 that differs by not more than a total of three, two, or in particular one amino acid additions, substitutions, and/or deletions from a heavy chain CDR1 having an amino acid sequence as shown in SEQ ID NO: 7 (TASGFSLSRYWMT),
   (b2) a heavy chain CDR2 that differs by not more than a total of three, two, or in particular one amino acid additions, substitutions, and/or deletions from a heavy chain CDR2 having an amino acid sequence as shown in SEQ ID NO: 8 (RSGNTYFADWAKG), and/or
   (b3) a heavy chain CDR3 that differs by not more than a total of three, two, or in particular one amino acid additions, substitutions, and/or deletions from a heavy chain CDR3 having an amino acid sequence as shown in SEQ ID NO: 9 (GGQNNGYDL),
or
both the light chain variable domain as defined under (a) and the heavy chain variable domain as defined under (b).

Alternatively or additionally, the monoclonal antibody, or fragment thereof, of the present invention comprises (a) a light chain variable domain comprising
   (a1) a light chain CDR1 that differs by not more than a total of three, two, or in particular one amino acid additions, substitutions, and/or deletions from a light chain CDR1 having an amino acid sequence as shown in SEQ ID NO: 4 (QSSESVYSNNFLS),
   (a2) a light chain CDR2 that differs by not more than a total of three, two, or in particular one amino acid additions, substitutions, and/or deletions from a light chain CDR2 having an amino acid sequence as shown in SEQ ID NO: 5 (EASKVAS), and (a3) a light chain CDR3 that differs by not more than a total of three, two, or in particular one amino acid additions, substitutions, and/or deletions from a light chain CDR3 having an amino acid sequence as shown in SEQ ID NO: 6 (AGGYDVSDDA), and (b) a heavy chain variable domain comprising (b1) a heavy chain CDR1 that differs by not more than a total of three, two, or in particular one amino acid additions, substitutions, and/or deletions from a heavy chain CDR1 having an amino acid sequence as shown in SEQ ID NO: 7 (TASGFSLSRYWMT), (b2) a heavy chain CDR2 that differs by not more than a total of three, two, or in particular one amino acid additions, substitutions, and/or deletions from a heavy chain CDR2 having an amino acid sequence as shown in SEQ ID NO: 8 (RSGNTYFADWAKG), and (b3) a heavy chain CDR3 that differs by not more than a total of three, two, or in particular one amino acid additions, substitutions, and/or deletions from a heavy chain CDR3 having an amino acid sequence as shown in SEQ ID NO: 9 (GGQNNGYDL).

In an aspect, the monoclonal antibody, or fragment thereof, of the present invention comprises (a) a light chain variable domain comprising (a1) a light chain CDR1 comprising at least 11, in particular at least 12 consecutive amino acids of the amino acid sequence as shown in SEQ ID NO: 4 (QSSESVYSNNFLS), (a2) a light chain CDR2 comprising at least 5, in particular at least 6 consecutive amino acids of the amino acid sequence as shown in SEQ ID NO: 5 (EASKVAS), and/or (a3) a light chain CDR3 comprising at least 8, in particular at least 9 consecutive amino acids of the amino acid sequence as shown in SEQ ID NO: 6 (AGGYDVSDDA), and/or (b) a heavy chain variable domain comprising (b1) a heavy chain CDR1 comprising at least 11, in particular at least 12 consecutive amino acids of the amino acid sequence as shown in SEQ ID NO: 7 (TASGFSLSRYWMT), (b2) a heavy chain CDR2 comprising at least 11, in particular at least 12 consecutive amino acids of the amino acid sequence as shown in SEQ ID NO: 8 (RSGNTYFADWAKG), and/or (b3) a heavy chain CDR3 comprising at least 7, in particular at least 8 consecutive amino acids of the amino acid sequence as shown in SEQ ID NO: 9 (GGQNNGYDL).

In an aspect, the monoclonal antibody, or fragment thereof, of the present invention comprises (a) a light chain variable domain comprising (a1) a light chain CDR1 having a sequence as shown in SEQ ID NO: 4 (QSSESVYSNNFLS), (a2) a light chain CDR2 having a sequence as shown in SEQ ID NO: 5 (EASKVAS), and/or (a3) a light chain CDR3 having a sequence as shown in SEQ ID NO: 6 (AGGYDVSDDA), and/or (b) a heavy chain variable domain comprising (b1) a heavy chain CDR1 having a sequence as shown in SEQ ID NO: 7 (TASGFSLSRYWMT), (b2) a heavy chain CDR2 having a sequence as shown in SEQ ID NO: 8 (RSGNTYFADWAKG), and/or (b3) a heavy chain CDR3 having a sequence as shown in SEQ ID NO: 9 (GGQNNGYDL).

In an aspect, the monoclonal antibody, or fragment thereof, of the present invention comprises (a) a light chain variable domain comprising (a1) a light chain CDR1 having a sequence as shown in SEQ ID NO: 4 (QSSESVYSNNFLS), (a2) a light chain CDR2 having a sequence as shown in SEQ ID NO: 5 (EASKVAS), and (a3) a light chain CDR3 having a sequence as shown in SEQ ID NO: 6 (AGGYDVSDDA), and (b) a heavy chain variable domain comprising (b1) a heavy chain CDR1 having a sequence as shown in SEQ ID NO: 7 (TASGFSLSRYWMT), (b2) a heavy chain CDR2 having a sequence as shown in SEQ ID NO: 8 (RSGNTYFADWAKG), and (b3) a heavy chain CDR3 having a sequence as shown in SEQ ID NO: 9 (GGQNNGYDL).

Also preferably, the monoclonal antibody, or fragment thereof, which binds to CSF-1R (Colony stimulating factor 1 receptor) comprises a light chain variable domain that is, in increasing order of preference at least 70%, 75%, 80%, 85%, 90%, 95%, 98%, 99% or 100% identical to the light chain variable domain having a sequence as shown in SEQ ID NO: 2, and/or a heavy chain variable domain that is at least 70%, 75%, 80%, 85%, 90%, 95%, 98%, 99% or 100% identical to the heavy chain variable domain having a sequence as shown in SEQ ID NO: 3, wherein the light chain variable domain comprises (a1) a light chain CDR1 that differs by not more than a total of three, two, or in particular one amino acid additions, substitutions, and/or deletions from a light chain CDR1 having an amino acid sequence as shown in SEQ ID NO: 4 (QSSESVYSNNFLS), (a2) a light chain CDR2 that differs by not more than a total of three, two, or in particular one amino acid additions, substitutions, and/or deletions from a light chain CDR2 having an amino acid sequence as shown in SEQ ID NO: 5 (EASKVAS), and (a3) a light chain CDR3 that differs by not more than a total of three, two, or in particular one amino acid additions, substitutions, and/or deletions from a light chain CDR3 having an amino acid sequence as shown in SEQ ID NO: 6 (AGGYDVSDDA), and wherein the a heavy chain variable domain comprises (b1) a heavy chain CDR1 that differs by not more than a total of three, two, or in particular one amino acid additions, substitutions, and/or deletions from a heavy chain CDR1 having an amino acid sequence as shown in SEQ ID NO: 7 (TASGFSLSRYWMT), (b2) a heavy chain CDR2 that differs by not more than a total of three, two, or in particular one amino acid additions, substitutions, and/or deletions from a heavy chain CDR2 having an amino acid sequence as shown in SEQ ID NO: 8 (RSGNTYFADWAKG), and (b3) a heavy chain CDR3 that differs by not more than a total of three, two, or in particular one amino acid additions, substitutions, and/or deletions from a heavy chain CDR3 having an amino acid sequence as shown in SEQ ID NO: 9 (GGQNNGYDL).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity. Preferably, standard parameters are applied for determining the degree of sequence identity of two sequences. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BEST-FIT, BLAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. In an embodiment, the percent identity between two amino acid sequences is determined using the Needleman and Wunsch algorithm (Needleman 1970, J. Mol. Biol. (48):444-453) which has been incorporated into the needle program in the EMBOSS software package (EMBOSS: The European Molecular Biology Open Software Suite, Rice, P., Longden, I., and Bleasby, A., Trends in Genetics 16(6), 276-277, 2000), a BLOSUM62 scoring matrix, and a gap opening penalty of 10 and a gap entension pentalty of 0.5. A preferred, non-limiting example of parameters to be used for aligning two amino acid sequences using the needle program are the default parameters, including the EBLOSUM62 scoring matrix, a gap opening penalty of 10 and a gap extension penalty of 0.5.

The term "antibody" refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as goats, rabbits and mice, as well as non-mammalian species, such as shark immunoglobulins. For example, the antibody may be a rabbit antibody. The term "antibody" includes intact immunoglobulins and "antibody fragments" or "antigen binding fragments" that specifically bind to a molecule of interest (or a group of highly similar molecules of interest) to the substantial exclusion of binding to other molecules. The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, 111); Kuby, J., Immunology, 3rd Ed., W.H. Freeman & Co., New York, 1997.

In particular, the term "antibody" refers to a polypeptide ligand comprising at least a light chain and heavy chain immunoglobulin variable region which specifically recognizes and binds an epitope of an antigen. Antibodies are composed of a heavy and a light chain, each of which has a variable region, termed the variable heavy (VH) region and the variable light (VL) region. Together, the VH region and the VL region are responsible for binding the antigen recognized by the antibody. Typically, the antibody of the present invention has heavy (H) chains and light (L) chains interconnected by disulfide bonds. The term "light chain" as used herein includes a full-length light chain and fragments thereof having a sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains. The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$, The $V_H$ domain is at the amino-terminus of the polypeptide, and the $C_H$ domains are at the carboxyl-terminus, with the $C_H3$ being closest to the carboxy-terminus of the polypeptide, There are five main heavy chain classes (or isotypes) which determine the functional activity of an antibody molecule: IgM, IgD, IgG, IgA and IgE. Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. An antibody that binds CSF-1R will have a specific VH region and the VL region sequence, and thus specific CDR sequences.

The antibody, or fragment thereof, of the present invention may be a single chain antibody, an IgD antibody, an IgE antibody, an IgM antibody, an IgG antibody and fragments thereof. For example, the antibody may be an IgG antibody such as an IgG1 antibody; an IgG2 antibody; an IgG3 antibody; or an IgG4 antibody. In an embodiment, the antibody, or fragment thereof, has been produced recombinantly.

Also encompassed by the present invention are fragments of the monoclonal antibody of the present invention. The fragment shall be an immunologically functional fragment, i.e. an antigen-binding fragment. Accordingly, the fragment of the monoclonal antibody of the present invention shall be capable of the binding CSF-1R, such as human CSF-1R. Accordingly, the term "immunologically functional fragment" of an antibody, as used herein, refers to a portion of an antibody that lacks at least some of the amino acids present in a full-length chain but which is capable of specifically binding to CSF-1R. Immunologically functional immunoglobulin fragments include Fab, Fab', $F(ab')_2$, and Fv fragments. How to produce antigen-binding fragments is well-known in the art. For example, the fragments can be produced by enzymatic cleavage of an antibody of the present invention. In addition, the fragments can be generated by synthetic or recombinant techniques. Fab fragments are preferably generated by papain digestion of an antibody, Fab' fragments by pepsin digestion and partial reduction, F(ab')2 fragments by pepsin digestion. Fv fragments are preferably produced by molecular biology techniques.

The fragment of an antibody may also be a diabody, which are small antibody fragments with two antigen-binding sites. Diabodies preferably comprise a heavy chain variable domain connected to a light chain variable domain in the same polypeptide chain.

The antibody of the present invention is preferably a monoclonal antibody. As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells.

In an embodiment, the antibody of the present invention is an isolated antibody. Thus, the antibody shall be an antibody which has been purified. Purification of an antibody can be achieved by methods well-known in the art such as Size Exclusion Chromatography (SEC). Accordingly, the antibody shall have been isolated from the cells in which the antibody was produced. In some embodiments, an isolated antibody is purified to greater than 70% by weight of antibody as determined by, for example, the Lowry method, and in some embodiments, to greater than 80%, 90%, 95%, 96%, 97%, 98% or 99% by weight. In one preferred embodiment the isolated antibody according to the present invention is purified to greater than 90% purity as determined by SDS-PAGE under reducing conditions using Coomassie blue staining for protein detection.

The monoclonal antibody of the present invention, or fragment thereof, shall specifically bind to the CSF-1R polypeptide, e.g. to the human CSF-1R polypeptide. The expression "binding" and "specifically binding" are well understood and are used to indicate that an antibody (or fragment thereof) does not significantly bind to other biomolecules.

Preferably, the antibody of the present invention (or fragment thereof) shall specifically bind to the intracellular domain of the CSF-1R polypeptide, in particular to the kinase domain. The epitope of the monoclonal antibody, or fragment thereof, preferably comprises a sequence as shown in SEQ ID NO: 1 (YKNIHLEKKY). SEQ ID NO: 1 corresponds to the amino acids 699 to 708 of human CSF-1R (see SEQ ID NO: 10). Thus, the monoclonal antibody of the present invention, or the fragment thereof, shall specifically bind to this region. Preferably, at least one of the two Tyrosine residues of said epitope is phosphorylated, i.e. the Tyrosine residue at position 699 or the Tyrosine residue at position 708. More preferably, both Tyrosine residues of said epitope are phosphorylated, i.e. the Tyrosine residue at position 699 and the Tyrosine residue at position 708. Accordingly, it is envisaged that the antibody of the present invention, or fragment thereof, binds the human CSF-1R polypeptide, wherein the Tyrosine residue at position 699 and/or the Tyrosine residue at position 708 is/are phosphorylated.

The term "epitope" denotes a protein determinant capable of specifically binding to an antibody. Thus, the term preferably refers to the portion of the CSF-1R polypeptide (such as the human CSF-1R polypeptide) capable of being specifically bound by the antibody of the present invention (or the fragment thereof). Epitopes usually consist of chemically active surface groupings of molecules such as amino acids and usually epitopes have specific three-dimensional structural characteristics, as well as specific charge characteristics. Conformational and nonconformational epitopes are distinguished in that the binding to the former but not the latter is lost in the presence of denaturing solvents.

In a preferred embodiment, the antibody of the present invention or the fragment thereof is linked to a detectable label. A detectable label as described herein is preferably a label which is not naturally linked to an antibody or antigen-binding fragment thereof. Thus, the detectable label is preferably heterologous with respect to the antibody. Suitable labels are any labels detectable by an appropriate detection method. In an embodiment said detectable label is an enzyme, biotin, a radioactive label, a fluorescent label, a chemiluminescent label, an electrochemiluminescent label, a gold label, or a magnetic label.

Enzymatic labels include e.g. horseradish peroxidase, alkaline phosphatase, beta-galactosidase, and luciferase. The substrates for these enzymes are well-known in the art. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate). A suitable enzyme-substrate combination may result in a colored reaction product, fluorescence or chemoluminescence, which can be measured according to methods known in the art. Fluorescent labels, e.g., include 5-carboxyfluorescein, fluorescein isothiocyanate, rhodamine, tetramethylrhodamine, Cy2, Cy3, and Cy5, fluorescent proteins such as GFP (Green Fluorescent Protein), Texas Red and the Alexa dyes. Radioactive labels, e.g., include radioactive isotopes of iodide, cobalt, selenium, tritium, carbon, sulfur and phosphorous. A radioactive label can be detected by any method known and appropriate, e.g. a light-sensitive film or a phosphor imager. Magnetic labels e.g. include paramagnetic and superparamagnetic labels. Chemiluminescent labels of use may include luminol, iso-luminol, an aromatic acridinium ester, an imidazole, an acridinium salt or an oxalate ester.

The definition and explanations given herein above, preferably, apply mutatis mutandis to the following.

The antibody of the present invention, or antigen-binding fragment thereof, is useful in methods relating to the localization and/or quantitation of CSF-1R polypeptide. For example, the antibody, or fragment thereof, allows for determining the amount of the CSF-1R polypeptide in a sample, for use in diagnostic methods, or for imaging the CSF-1R polypeptide.

Accordingly, the present invention is directed to a method for detecting CSF-1R in a sample, comprising (a) contacting a sample comprising CSF-1R with the monoclonal antibody, or fragment thereof, of any one of the present invention, thereby forming a complex comprising CSF-1R and said monoclonal antibody, or fragment thereof, and (b) detecting the complex formed in step (a), thereby detecting CSF-1R in said sample.

The "subject" as referred to herein is, preferably, a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the subject is a mammalian subject, such as a human subject. In some aspects of the method, the sample is obtained from a subject that is diagnosed as having, suspected as having, or at risk of having cancer.

The term "sample" as used herein is intended to include tissues, cells and biological fluids isolated from a subject, as well as tissues, cells, and fluids present within a subject. Biological samples of the present disclosure include, e.g., but are not limited to, whole blood, plasma, semen, saliva, tears, urine, fecal material, sweat, buccal, skin, cerebrospinal fluid, and hair. Biological samples can also be obtained from biopsies of internal organs or from cancers.

In an embodiment, the sample contains cancer cells. Cancer cells are cells that have undergone a malignant transformation that makes them pathological to the patient. The term "cancer cell", as used herein, includes not only a primary cancer cell, but also any cell derived from a cancer cell ancestor. This includes metastasized cancer cells, and in vitro cultures and cell lines derived from cancer cells.

Preferably, the sample containing cancer cells is biopsy tissue containing cancer cells. Thus, the sample has been obtained from a subject who suffers from cancer.

In accordance with the present invention, the sample has been obtained from a subject who has been contacted with candidate compound for the treatment of cancer. Thus, said candidate compound has been administered to the subject, in particular a subject suffering from cancer, before obtaining the sample to be tested. Alternatively, the sample has been contacted with a candidate compound for the treatment of cancer.

In an embodiment, the candidate compound for the treatment of cancer is an inhibitor of CSF-1R such as a small molecule inhibitor or a monoclonal antibody which binds CSF-1R, such as a monoclonal antibody which binds the extracellular domain of CSF-1R.

In an embodiment, the inhibitor of CSF-1R is selected from xidartinib, PLX7486, ARRY-382, JNJ-40346527, BLZ945, Emactuzumab, AMG820, and IMC-CS4 (see Cannarile et al., 2017 Journal for Immunotherapy of Cancer. 5 (1): 53).

In an embodiment of the above method, the detection of CSF-1R is the quantitative detection of CSF-1R. Thus, the amount of the CSF-1R in the sample is determined. The determined amount of CSF-1R may be compared to the amount of CSF-1R in a control biological sample. Thus, it may be e.g. assessed whether the amount of CSF-1R in the test sample is increased or decreased as compared to the control sample.

In an alternative embodiment of the above method, the detection of CSF-1R is the immunohistochemical detection of CSF-1R. Thus, CSF-1R is identified within the context of intact cells by labeling the test sample with the antibody (of antigen-binding fragment thereof) of the present invention in a manner that can be visualized on a microscope. By identifying CSF-1R in the context of a tissue environment or cellular environment, spatial relationships between the biomarkers and other morphological or molecular features of the cell or tissue sample can be elucidated, which may reveal information that is not apparent from other molecular or cellular techniques.

For detecting CSF-1R, the antibody of the present invention (or fragment thereof) may comprise a detectable label as described elsewhere herein.

The present invention is further directed to the in vitro use of the monoclonal antibody, or fragment thereof, of the present invention for the detection of CSF-1R, such as human CSF-1R in a sample.

The term "sample" and "subject" has been defined above. The sample is a cancer cell or cancer tissue. The definitions apply accordingly. As described above, the sample may have been contacted with a candidate compound for the treatment of cancer. Alternatively, the sample has been obtained from a subject who has been contacted with said candidate compound.

The present invention also relates to a complex comprising the monoclonal antibody, or fragment thereof, of the present invention and CSF-1R. Typically, the monoclonal antibody, or fragment thereof, is bound to CSF-1R (such as human CSF-1R) in said complex.

In an embodiment of the method and use of the present invention, the native form of CSF-1R (such as human CSF-1R) is detected. Thus, undenatured CSF-1R is detected. In an alternative embodiment, denatured CSF-1R is detected. Accordingly, the sample may have been subjected to at least one pre-treatment step which results in the denaturation of CSF-1R. E.g. the sample may have been subjected to heat, or at least one denaturing agent has been added to the sample.

The present invention also relates to a host cell producing the antibody of the present invention, or the antigen-binding fragment thereof. In a preferred embodiment, the host producing the antibody of the present invention is a hybridoma cell. Moreover, the host cell may be any kind of cellular system which can be engineered to generate the antibodies according to the current invention. For example, the host cell may be an animal cell, in particular a mammalian cell. In one embodiment HEK293 (human embryonal kidney cells) such as HEK 293-F cells as used in the Examples section, or CHO (Chinese hamster ovary) cells are used as host cells. In another embodiment, the host cell is a non-human animal or mammalian cell.

The host cell preferably comprises at least one polynucleotide encoding for the antibody of the present invention, or fragment thereof. For example, the host cell comprises at least one polynucleotide encoding for the light chain of the antibody of the present invention and at least one polynucleotide encoding the heavy chain of the antibody of the present invention. Said polynucleotide(s) shall be operably linked to a suitable promoter.

The invention further relates to a pharmaceutical composition comprising the monoclonal antibody, or fragment thereof, of the invention and a pharmaceutically acceptable diluent, solvent, carrier, salt and/or adjuvant.

The invention provides for an in vivo or in vitro method for decreasing CSF-1R expression in a target cell which is expressing CSF-1R, said method comprising administering an the monoclonal antibody, or fragment thereof, or pharmaceutical composition of the invention in an effective amount to said cell.

The invention provides for a method for treating or preventing a disease comprising administering a therapeutically or prophylactically effective amount of the monoclonal antibody, or fragment thereof, or pharmaceutical composition of the invention to a subject suffering from or susceptible to the disease. In some embodiments, the disease is cancer.

The invention provides monoclonal antibody, or fragment thereof, or pharmaceutical composition of the invention for use in medicine.

The invention provides for the monoclonal antibody, or fragment thereof, or pharmaceutical composition of the invention for use in the treatment or prevention of a cancer.

The invention provides for the use of the monoclonal antibody, or fragment thereof, or pharmaceutical composition of the invention, for the preparation of a medicament for treatment or prevention of cancer.

The Figures show:

FIG. 1 Circular Dichroism Analyses. Temperature ramp up/down experiment with the TtSlyD-CSF1R immunogen. TtSlyD-CSF1R is at least stable until 60° C. and restructures when cooling.

FIG. 2 Circular Dichroism Analyses of the immunogen TtSlyD-CSF1R before and after heating/cooling. TtSlyD-CSF1R restructures after thermal denaturation.

Figure 3:
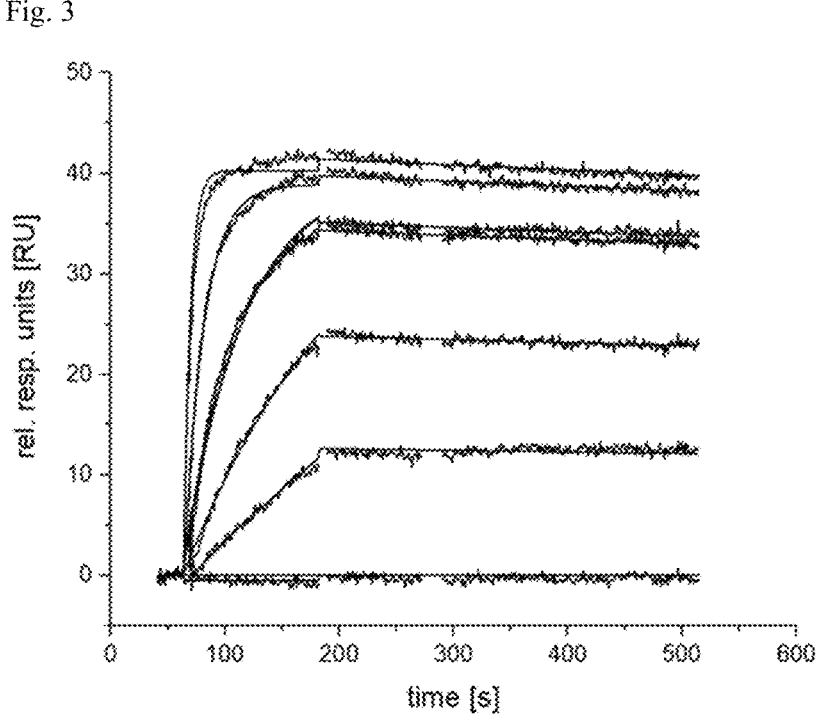

FIG. 3 Biacore Sensorgram showing concentration-dependent kinetics of captured antibody 1H11 versus phosphorylated TtSlyD-CSF1R as analyte in solution, Overlay of analyte concentrations and Langmuir Fitting model (straight black lines). Affinity $K_D$ 0.2 nM, $k_a$ 5.78 E+05 1/Ms, $k_d$ 1.22 E-04 1/s.

Figure 4:
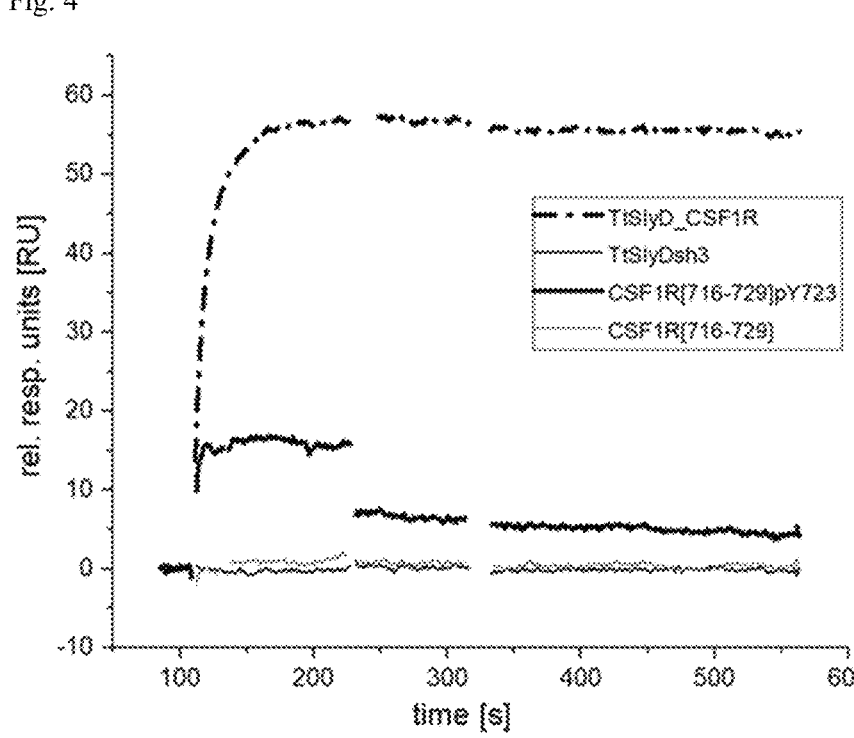

FIG. 4 Biacore Sensorgram showing an overlay of 300 nM single analyte concentration injections of four analytes in solution. Highest signal amplitude was found with the analyte TtSlyD-CSF1R (dashed line), Second highest signal response with the analyte pY723 phosphorylated peptide CSF1R[716-729] (thick black line). The negative control analytes are TtSlyDsh3 and the non-phosphorylated peptide CSF1R[716-729] (grey) with just background binding signal level. Antibody 1H11 shows phosphotyrosine-specific epitope binding properties.

Figure 5:
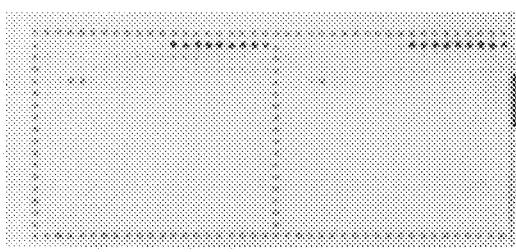

FIG. 5 CelluSpots™ epitope mapping technology. Right: glass slide with CSF-1R 15-mer peptides in duplicate. Left: CSF-1R peptide sequences are given as single amino acid code. pY means phosphorylated tyrosin:

SEQ ID NO: 13: P-E-G-G-V-D-pY-K-N-I-H-L-E-K-K,

SEQ ID NO: 14: E-G-G-V-D-pY-K-N-I-H-L-E-K-K-pY

SEQ ID NO 15: G-G-V-D-pY-K-N-I-H-L-E-K-K-pY-V

SEQ ID NO 16: G-V-D-pY-K-N-I-H-L-E-K-K-pY-V-R

SEQ ID NO 17: V-D-pY-K-N-I-H-L-E-K-K-pY-V-R-R

SEQ ID NO 18: D-pY-K-N-I-H-L-E-K-K-pY-V-R-R-D

SEQ ID NO 19: pY-K-N-I-H-L-E-K-K-pY-V-R-R-D-S

SEQ ID NO 20: K-N-I-H-L-E-K-K-pY-V-R-R-D-S-G

SEQ ID NO 21: N-I-H-L-E-K-K-pY-V-R-R-D-S-G-F

The 1H11 epitope sequence was determined by a single amino acid step analysis through the CSF-1R sequences.

Figure 6:
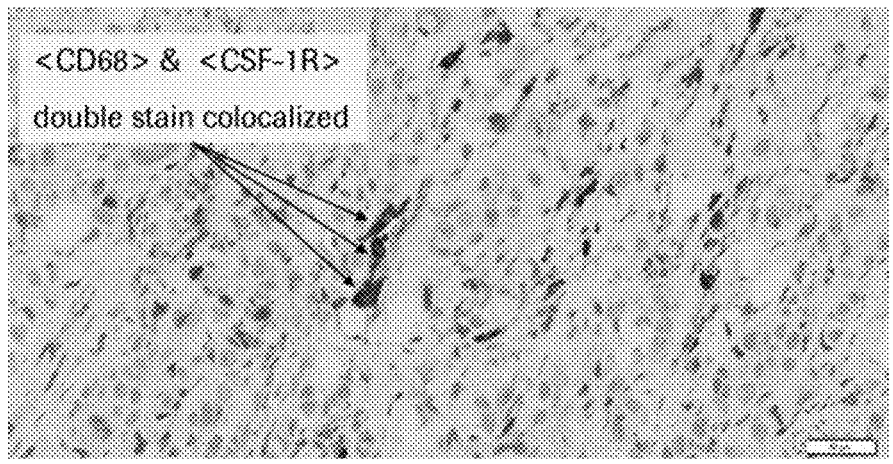

FIG. 6 IHC double stain. As compared to other antibodies that were isolated in the studies underlying the present invention that showed only a weak staining (not shown), the antibody 1H11 showed a very strong staining.

Figure 7:
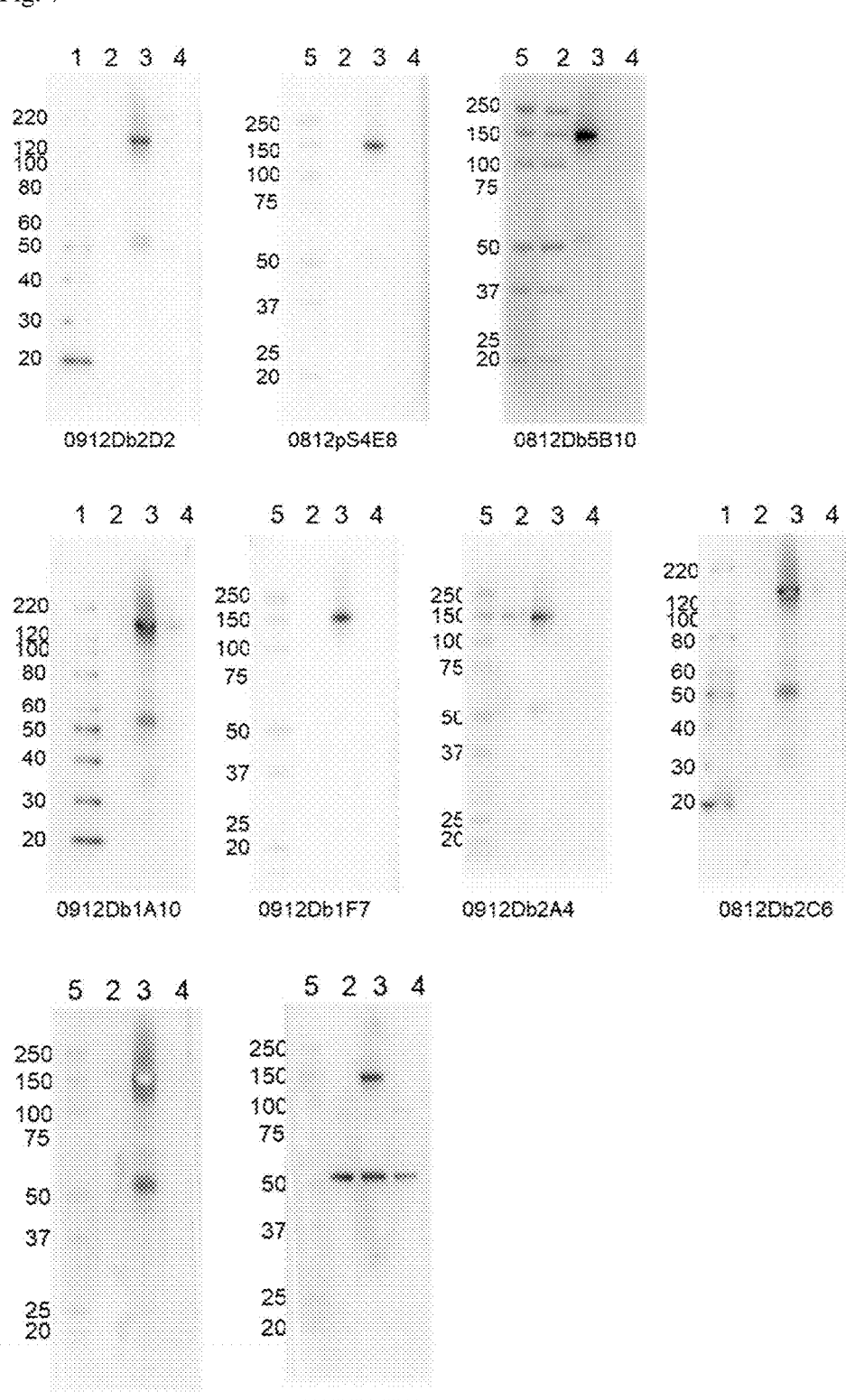
Figure 7:
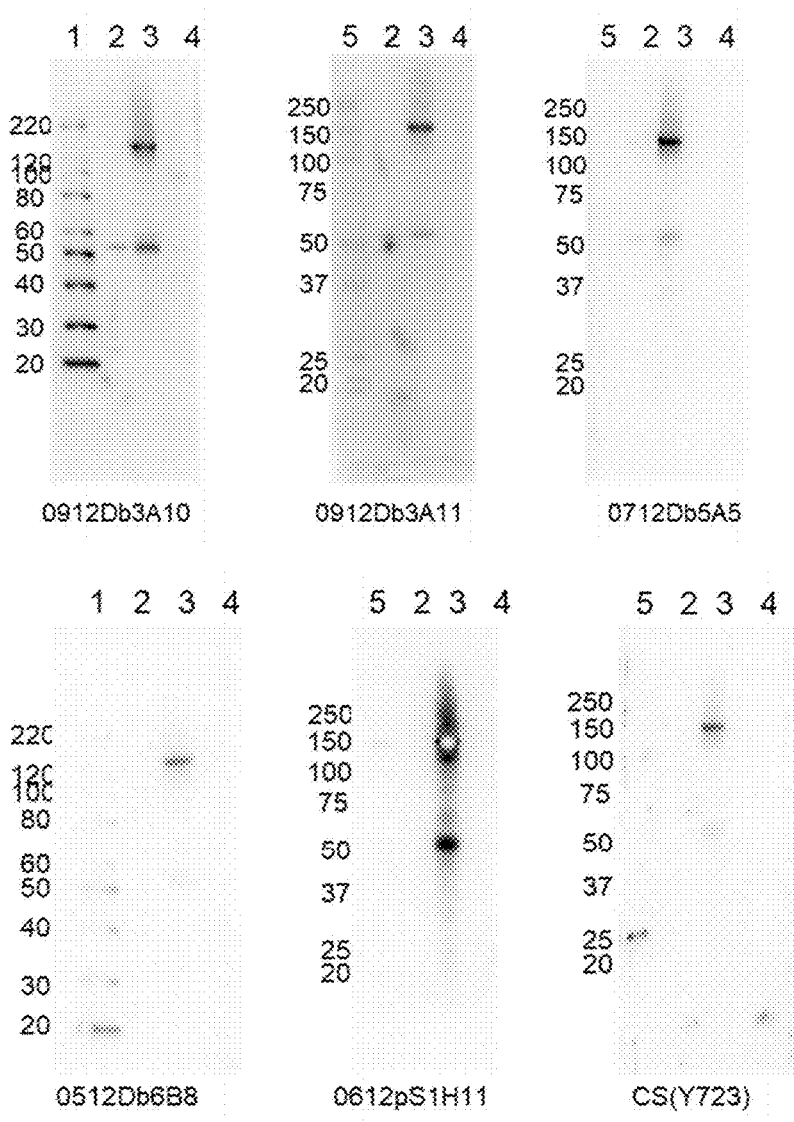

FIG. 7 Western-Blot analysis of selected antibodies. (lane 1: Western Standard; lane 2: NIH3T3 wt; lane 2 NIH 3T3+CSF1 K4; lane 4: NIH 3T3+CSF1 K8, lane 5: protein standards). Antibody 1H11 showed the strongest staining and overexposed the blot. The other tested antibodies showed a weak staining only.

EXAMPLES

The invention will be merely illustrated by the following Examples. The said Examples shall, whatsoever, not be construed in a manner limiting the scope of the invention.

Example 1: Preparation of the Immunogen

TtSlyD-CSF1R and TtSlyD-sh3 ORFs were synthetized by GeneArt and delivered within an ampicillin resistance cloning vector. TtSlyD-CSF1R encodes the amino acids sequence:

```
>TtSlyD-CSF1R
                              (SEQ ID NO: 11)
MRSKVGQDKV VTIRYTLQVE GEVLDQGELS YLHGHRNLIP

GLEEALEGRE EGEAFQAHVP AEKAYGAGSM LGPSLSPGQD

PEGGVDYKNI HLEKKYVRRD SGFSSQGVDT YVEMRPVSTS

SNDSFSEQDL DKEDGRPGSS GKDLDFQVEV VKVREATPEE

LLHGHAHGGG SRPLLPPLPG GGSRKHHHHH HHH
```

TtSlyD-sh3 was applied as insertion free control protein and encodes the amino acid sequence:

```
>TtSlyDsh3
                              (SEQ ID NO: 12)
MRSKVGQDKV VTIRYTLQVE GEVLDQGELS YLHGHRNLIP

GLEEALEGRE EGEAFQAHVP AEKAYGAGSG SSGKDLDFQV

EVVKVREATP EELLHGHAHG GGSRPLLPPL PGGGSRKHHH

HHHHH
```

Restriction Enzymes and "Rapid DNA Ligation Kit" were obtained from Roche. *E. coli* XL1-Blue Supercompetent Cell and BL21 Codon Plus were obtained from Stratagene. To purify the DNA "High Pure Plasmid Isolation Kit" and "High Pure PCR Product Purification Kit" (Roche) were used. pQE80L was used as cloning and expression vector.

The bacteria were grown in Lysogeny Broth (LB: 5 g/l Yeast Extract, 10 g/l Trypton, 5 g/l NaCl, pH7.0) with selection antibiotic (100 μg/ml Ampicillin). For improved growing during protein expression LB medium was exchanged to Super Broth medium (SB: 20 g/l Yeast Extract, 32 g/l Trypton, 5 g/l NaCl, pH7.0).

TtSlyD-CSF1R was released from the delivering vector with EcoRI and HindIII and ligated into the expression vector pQE80-L, the later digested with EcoRI and HindIII. After transformation of *E. coli* XL1-Blue bacteria, plasmidic DNA was obtained and transformed in *E. coli* BL21 Codon Plus. In brief, for recombinant expression and purification, cells were grown in SB medium at 37° C. When the exponential phase was reached, TtSlyD variants expression was induced using 0.5 mM isopropil-β-D-thiogalactoside (IPGT) for at least 3 h. Inclusion bodies from the cell pellet were resuspended in chilled sodium phosphate buffer (pH8.0) containing 7.0M GdmCl, and stirred for 2 h until complete cell lysis. The precleared lysate was applied into a Ni-NTA column and 10-15 column volumes of wash buffer (phosphate buffer pH8.0, 7.0M GdmCl, 10 mM imidazole) were applied. To avoid reactivation of copurifying proteases, a protease inhibitors cocktail (Complete EDTA-free, Roche) was included in the refolding buffer (phosphate buffer pH8.0, 20 mM imidazole). A total of 20-25 column volumes of refolding buffer were applied slowly over night. The inhibitors cocktail was removed, with 5-10 column volumes of further washing with refolding buffer, before eluting the protein in a gradient of 250 mM imidazole. Protein containing fractions were pooled and purified again through a size-exclusion chromatography column (HiLoad™ 26/60 Superdex™ 75 size exclusion chromatography column, Amersham Pharmacia) in Storage Buffer (50 mM $KH_2PO4$ pH6.95, 100 mM KCl, 0.5 mM EDTA). Only monomer containing fractions were recovered and assessed for purity in SDS denaturing gels. Novex® NuPAGE® SDS-PAGE Gel Systems (Invitrogen) were used for Western Blot analysis. Commassie-like protein staining was performed using SimplyBlue™ Safe-Stain (Invitrogen). Protein concentration measurements were performed with a DU®7400 Spectrophotometer (Beckman Coulter™). The molar extinction coefficients ($\varepsilon_{280}$) for fusion proteins were calculated by bioinformatics

Example 2: Circular Dichroism Spectra Analysis

Protein concentration measurements were performed with a DU®7400 Spectrophotometer (Beckman Coulter™). The molar extinction coefficients ($\varepsilon_{280}$) for fusion proteins were calculated by bioinformatics.

Near-UV CD spectra were recorded using a Jasco-720 spectropolarimeter with a thermostatic cell holder set to 20° C. and converted to mean residue ellipticity. The buffer was 50 mM potassium phosphate (pH6.95), 100 mM KCl and 0.5 mM EDTA. The spectra was recorded between 330-250 nm with a path length of 0.2 cm, and the protein concentration was 500 μM. The bandwidth was 1 nm, the scanning speed was 20 nm/min at a resolution of 0.5 nm, and the response was 1 s. To improve the signal to noise ratio, spectra were measured nine times and averaged. FAr-UV CD spectra were recorded using a Jasco-720 spectropolarimeter with a thermostatic cell holder set to 20° C. and converted to mean residue ellipticity. The buffer was 10 mM potassium phosphate (pH6.95) and 10 mM KCl. The spectra was recorded between 250-190 nm with a path length of 0.2 cm, and the protein concentration was 5 μM. The bandwidth was 1 nm, the scanning speed was 20 nm/min at a resolution of 0.5 nm, and the response was 1 s. To improve the signal to noise ratio, spectra were measured nine times and averaged.

For the thermal unfolding transitions of fusion proteins, the proteins were measured at 500 μM in 50 mM potassium phosphate (pH6.95), 100 mM KCl and 0.5 mM EDTA. Thermally induced unfolding-refolding transitions were recorded at 278 nm, and the path length of the cuvette was 0.2 cm. Heating and cooling rages were 1° C./min, and the response time was 4 s. To assess the reversibility of the unfolding, near-UV CD spectra of the fusion proteins were recorded before and after the thermally induced unfolding-refolding cycle.

Protein concentration measurements were performed with a DU®7400 Spectrophotometer (Beckman Coulter™). The molar extinction coefficients ($\varepsilon_{280}$) for fusion proteins were calculated by bioinformatics according to Gasteiger et al 2005.

Fluorescence spectra were recorded using a Cary Eclipse fluorescence spectrophotometer (Varian) with a thermostatic cell holder set to 20° C. The buffer was 50 mM potassium phosphate (pH6.95), 100 mM KCl and 0.5 mM EDTA. The samples were excited at 280/290/295 nm and the spectra were recorded between 300-425 nm with a path length of 1 cm. The protein concentration was 10-30 μM. The bandwidth was 5 nm, the scanning speed was 120 nm/min at a resolution of 1 nm, and the response was 0.5 s.

For the thermal unfolding transitions of fusion proteins, the same concentration and buffer were used. The full spectra were recorded for thermally induced unfolding transitions, with the same specifications as for single measurements. Heating intervals were set to 5° C., and the stabilization period between temperature changes was set to 10 min. To assess the reversibility of the unfolding, fluorescence spectra of the fusion proteins were recorded before and after the thermally induced unfolding-refolding cycle.

Example 3: Phosphorylation and Purification of TtSlyD-CSF1R

Buffer components were obtained from Merck, Roche and Sigma. Src (1-530) active kinase was purchased from Upstate (Millipore). According to manufacture instructions Src kinase was diluted (20 mM MOPS-NaOH pH7.0, 1 mM EDTA, 0.01% Brij-30, 5% glycerol, 0.1% 3-mercaptoethanol and 1 mg/ml BSA), aliquoted and stored at −80° C. Novex® NuPAGE® SDS-PAGE Gel Systems (Invitrogen) were used for Western Blot analysis. To detect phosphorylated protein, several pan-pTyr primary antibodies were used: P-Tyr-4G10 (Millipore), P-Tyr-100 and P-Tyr-102 (Cell Singaling), and an HRP-conjugated goat-anti-mouse-IgG (Invitrogen) as secondary. The results were analyzed by ChemiDoc™ MP (Bio-Rad), incubating the membrane with Lumi-Light PLUS Western Blotting Substrate (IRoche).

4.5 mg TtSlyD-CSF1R was diluted to a 60 μM concentration with reaction buffer (10 mM MOPS-NaOH pH7.0, 50 mM NaCl, 0.3 mM EDTA, 0.001% Brij-30, 0.5% glycerol, 10 mM MgAc, 0.1 mM ATP, 0.25 mM orthovanadate and 0.1 mg/ml BSA). 4 units of Src were added (1.97 U/μg) and the reaction was incubated for 2 h at 30° C. Afterwards the reaction was stopped by chelating $Mg^{2+}$ cations using EDTA. To remove the buffer and contaminating proteins, the solution was loaded in a HiLoad™ 16/60 Superdex™ 200 size exclusion chromatography column (Amersham, Pharmacia) using sterile-filtrated PBS pH6.95 as a sheath solution. TtSlyD-CSF1R containing fractions were recovered and the protein was concentrated using Ultracell™ 10 k Amicon (Millipore). 81% of the initial protein was recovered.

Example 4: Rabbit Monoclonal Antibody Production

Rabbits were immunized subcutaneous each 30 days with 100 μg antigen. Serum was taken starting at day 45 and the antibody titers against the antigens were tested. After 2 month the immunogen titer was over 200.000. Peripheral blood was monthly taken 5 to 6 days after the boost. The blood was treated with citrate to avoid coagulation, and was freshly processed the same day. The Peripheral Blood Mononuclear Cells (PBMCs) were required for either obtaining antibody-producing B-cells or macrophages for their secreted grown factors. PBMCs were obtained from peripheral rabbit blood and antigen specific monoclonal antibodies were generated as it is described in Seeber et al. (2014), PLoS One. 2014 Feb. 4; 9(2). 5.10e7 PMBCs/ml were resuspended in FACS Puffer (PBS+0.1% BSA) with 250 nM of the biotinylated antigen. After 15-20' incubation at 4° C., the cells were washed with 40 ml PBS, and resuspended to 10e8 PMBCs/ml in Labeling Buffer (PBS+2 mM EDTA). 10% volume of Streptavidin Beads was added (MACS Miltenyi Biotec) and they were incubated 15-20' at 4° C. The cells were washed with 40 ml PBS, and resuspended to 2.10e8 PMBCs/ml in MACS Buffer (PBS+2 mM EDTA+0.5% BSA). The suspension was loaded in a pre-equilibrated MS Columns (MACS Mitenyi Biotec), washed with three volumes of MACS Buffer, and the bound cells were recovered in 1 ml MACS Buffer. To discriminate between cell types, the recovered cells were stained with a fluorescent antibody against rabbit IgG (AbD Serotec), and the IgG positive cells were single cell sorted using a FACSAria I cell sorter (BD Biosciences). The cells were incubated in B-cell medium as described in Seeber et al. for one week. After one week, the supernatant of the clones were tested for IgG production and antigen specificity using HitELISA techniques. The positive clones were selected and stored at −80° C. with RNA lysis buffer. HitELISAs with cell culture supernatans and purified mAbs. ELISA plates (Roche) were coated with 100-250 ng/ml of antigens in carbonate buffer, pH9.6. Biotinylated antigens were bound directly to Streptavidin coated plates (Roche) using the same antigen concentration. After washing, plates were blocked with Incubation Buffer (IB: 1% BSA 0.05% Tween-PBS). The plates were incubated with cell supernatants or purified mAbs diluted with IB. After washing, the plates were developed by incubation for 1 h with HRP-conjugated F(ab')2 fragment goat anti-rabbit IgG (Dianova) and adding 100 µl ABTS solution (Roche). Optical densities were measured at the appropriate wavelength using an ELISA microplate reader. IgG concentration sandwich-ELISA. ELISA plates were coated with 3 µg/ml of goat anti-rabbit IgG in carbonate buffer, pH9.6. After washing, plates were blocked with IB. The plates were incubated with cell supernatants diluted in D3. Subsequent ELISAs were performed similarly as described above.

The B-cell mRNA was purified with RNeasy® Plus Mini Kit (Qiagen®) from the positive single memory B-cells cultures frozen at −80° C. Reverse transcription was performed with Transcription Universal cDNA Master (Roche). The cDNA plates were stored at −20° C. until further use. The IgH, Igλ and Igκ variable genes were amplified independently by PCR with the appropriate primers, starting from 2 µl cDNA as a template with Expand High Fidelity PCR System (Roche). The purified single amplified bands and the plasmids containing the IgG constant regions were digested with T4 DNA Polymerase (Roche) to generate 5' overhangs, followed by RecA treatment (NE Biolabs) to be religated by Sequence and Ligation-Independent Cloning (SLIC). The recombined plasmids were transformed and tested for correct insertion cloning using standard digestion and sequencing protocols.

Full length IgG mAbs were produced by transient cotransfection of the paired heavy and light chain TIPE plasmids into FreeStyle 293-F cells (Invitrogen) grown in serum-free FreeStyle™ 293 Expression Medium (Gibco®Invitrogen) using 293-Free™ Transfection Reagent (Novagen®). Cells were cultivated one week at 37° C./5-8% $CO_2$ with continuous shaking at 180 rpm. The supernatants were collected by centrifugation and stored at −20° C.

Example 5: Interaction Analysis

A Biacore B3000 instrument (GE Healthcare) was used to kinetically assess the rabbit antibodies for kinetics and binding specificity for TtSlyD-CSF1R. A CMS series sensor was mounted into the system and was normalized in HBS-ET buffer (10 mM HEPES pH 7.4, 150 mM NaCl, 3 mM EDTA, 0.005% w/v Tween 20) according to the manufacturer's instructions. The sample buffer was the system buffer supplemented with 1 mg/ml CMD (Carboxymethyldextran, Sigma #86524). The system operated at 25° C. 10000 RU GAR<F(ab)2> (relative units of goat anti rabbit F(ab)2/ Jackson Laboratories, cat. No. 100018) were immobilized according to the manufacturer's instructions using EDC/ NHS chemistry on all flow cells. The sensor was saturated with 1M ethanolamine. The binding activity of the antibodies against the analytes were kinetically tested. Analytes in solution were two 2 kDa peptides CSF1R (716-729) with Y723 phosphorylated and non-phosphorylated, a 14 kDa TtSlyDsh3 control protein with a CSF1R unrelated insertion domain and the 21 kDa TtSlyD-CSF1R protein. Antibodies were captured by a 2 min injection at 10 µl/min of cell culture HEK supernatant diluted 1:2 in sample buffer. The flow rate was set to 100 µl/min. The analyte was injected at different concentration steps of 0 nM, 1.1 nM, 3.7 nM, 11.1 nM, 33.1 nM, 100 nM and 300 nM for 2 min. The dissociation was monitored for 5 min. Kinetic signatures were monitored and evaluated using the Biaevaluation Software and a binary Langmuir Fitting model with $R_{MAX}$ local. Acidic regeneration of the sensor surface was achieved using three consecutive injections of 10 mM Glycine pH 1.7 at 30 µl/min for 60 sec.

Example 6: Linear Epitope Mapping

Peptide based epitope mappings were carried out as described and commercially offered by Intavis, Cologne Germany, using the CelluSpots™ technology. Epitope mappings were carried out by means of a library of overlapping, immobilized peptide fragments (length: 15 amino acids) corresponding to the sequences of human CSF1R KID domain. Each peptide synthesized was shifted by one amino acid, i.e. it had 14 amino acids overlap with the previous and the following peptide, respectively. For preparation of the peptide arrays the Intavis CelluSpots™ technology was employed. In this approach, peptides are synthesized with an automated synthesizer (Intavis MultiPep RS) on modified cellulose disks which are dissolved after synthesis. The solutions of individual peptides covalently linked to macromolecular cellulose are then spotted onto coated microscope slides. The CelluSpots™ synthesis was carried out stepwise utilizing 9-fluorenylmethoxycarbonyl (Fmoc) chemistry on amino-modified cellulose disks in a 384-well synthesis plate. In each coupling cycle, the corresponding amino acids were activated with a solution of DIC/HOBt in DMF. Between coupling steps un-reacted amino groups were capped with a mixture of acetic anhydride, diisopropylethyl amine and 1-hydroxybenzotriazole. Upon completion of the synthesis, the cellulose disks were transferred to a 96-well plate and treated with a mixture of trifluoroacetic acid (TFA), dichloromethane, triisoproylsilane (TIS) and water for side chain deprotection. After removal of the cleavage solution, the cellulose bound peptides are dissolved with a mixture of TFA, TFMSA, TIS and water, precipitated with diisopropyl ether and re-suspended in DMSO. The peptide solutions were subsequently spotted onto Intavis CelluSpots™ slides using an Intavis slide spotting robot.

For linear epitope analysis, the slides prepared as described above were treated using the BenchMark XT Automated Slide Preparation System (Ventana). The slides were developed with OptiView DAB IHC Detection Kit plus OptiView Amplification Kit (Ventana), according to the standardized protocols. Briefly described, the slides were "wet-loaded" in the system, and blocked for 32 minutes with 1% BSA in Phosphate Buffer (PBS). The antibody was diluted to 1 µg/ml in Antibody Diluent (Ventana) and applied manually on the slide for 1 h at room temperature; both Amplifier and Amplification Multimer reagents were incubated for 8 minutes each without counterstain staining. To analyze the colorimetric staining, a ChemiDoc Analyzer (BioRAD) was used.

When a high signal was desired, the slides were treated manually with chemiluminiscent reagents. Briefly, the slides were washed with ethanol and then with Tris-buffered saline (TBS; 50 mM Tris, 137 mM NaCl, 2.7 mM KCl, pH 8) before blocking for 16 h at 4° C. with 5 mL 10× Western Blocking Reagent (Roche Applied Science), 2.5 g sucrose in TBS, 0.1% Tween 20. The slide was washed with TBS and 0.1% Tween 20 and incubated afterward with 1 µg/mL of the corresponding antibodies in TBS and 0.1% Tween 20 at ambient temperature for 2 h and subsequently washed with TBS+0.1% Tween 20. For detection, the slide was incubated with anti-rabbit/anti-mouse secondary HRP-antibody (1:20000 in TBS-T) followed by incubation with chemiluminescence substrate luminol and visualized with a Lumilmager (Roche Applied Science). ELISA-positive SPOTs were quantified and through assignment of the corresponding peptide sequences the antibody binding epitopes were identified.

Immunohistochemistry

Immunohistochemistry was performed using the BenchMark XT Automated Slide Preparation System (Ventana).

The slides were developed with iVIEW DAB Detection Kit (Ventana), according to the standardized protocols. Briefly described, the slides were deparafined with Cell Conditioning 1 (CC1, Ventana), and blocked for 32 minutes with 1% BSA in Phosphate Buffer (PBS). The antibody was diluted to 1 µg/ml in Antibody Diluent (Ventana) and applied manually on the slide for 1 h at room temperature.

---

The invention claimed is:

1. A monoclonal antibody, or fragment thereof, which binds to CSF-1R (Colony stimulating factor 1 receptor), wherein said monoclonal antibody, or fragment thereof, comprises: (a) a light chain variable domain having a sequence as shown in SEQ ID NO: 2, and (b) a heavy chain variable domain having a sequence as shown in SEQ ID NO: 3.

2. The monoclonal antibody, or fragment thereof, of claim 1, wherein CSF-1R is human CSF-1R.

3. The monoclonal antibody, or fragment thereof, of claim 1, wherein the epitope of the monoclonal antibody, or fragment thereof, comprises a sequence as shown in SEQ ID NO: 1 (YKNIHLEKKY).

4. The monoclonal antibody, or fragment thereof, of claim 3, wherein at least one of the two tyrosine residues of said epitope is phosphorylated.

5. The monoclonal antibody, or fragment thereof, of claim 4, wherein both tyrosine residues of said epitope are phosphorylated.

6. A monoclonal antibody, or fragment thereof, comprising:

(a) a light chain variable domain comprising
  (a1) a light chain CDR1 having a sequence as shown in
      SEQ ID NO: 4 (QSSESVYSNNFLS),
  (a2) a light chain CDR2 having a sequence as shown in
      SEQ ID NO: 5 (EASKVAS), and
  (a3) a light chain CDR3 having a sequence as shown in
      SEQ ID NO: 6 (AGGYDVSDDA),
and
(b) a heavy chain variable domain comprising
  (b1) a heavy chain CDR1 having a sequence as shown
      in SEQ ID NO: 7 (TASGFSLSRYWMT),
  (b2) a heavy chain CDR2 having a sequence as shown
      in SEQ ID NO: 8 (RSGNTYFADWAKG), and
  (b3) a heavy chain CDR3 having a sequence as shown
      in SEQ ID NO: 9 (GGQNNGYDL).

7. A method for detecting CSF-1R in a sample in vitro, comprising:
  (a) contacting the sample with the monoclonal antibody, or fragment thereof, of claim 1; and
  (b) detecting binding of said antibody to CSF-1R in the sample.

8. The method of claim 7, wherein
  (a) the sample has been contacted with a candidate compound for the treatment of cancer, or wherein the sample has been obtained from a subject who has been contacted with said candidate compound,
  (b) the sample is a cancer cell or cancer tissue,
  (c) the subject is a mammalian subject such as a human subject,
  (d) the detection of CSF-1R is the quantitative detection of CSF-1R, and/or
  (e) the detection of CSF-1R is the immunohistochemical detection of CSF-1R.

9. A method for detecting CSF-1R in a sample, comprising
  (a) contacting a sample comprising CSF-1R with the monoclonal antibody, or fragment thereof, of claim 1, thereby forming a complex comprising CSF-1R and said monoclonal antibody, or fragment thereof, and
  (b) detecting the complex formed in step (a), thereby detecting CSF-1R in said sample.

10. A complex comprising the monoclonal antibody, or fragment thereof, of claim 1 and CSF-1R.

11. The method of claim 7, wherein said CSF-1R comprises a phosphorylated tyrosine residue at a position which corresponds to position 699 of human CSF-1R and/or a phosphorylated tyrosine residue at a position which corresponds to position 708 of human CSF-1R.

12. The method of claim 8, wherein said CSF-1R comprises a phosphorylated tyrosine residue at a position which corresponds to position 699 of human CSF-1R and/or a phosphorylated tyrosine residue at a position which corresponds to position 708 of human CSF-1R.

13. The method of the method of claim 9, wherein said CSF-1R comprises a phosphorylated tyrosine residue at a position which corresponds to position 699 of human CSF-1R and/or a phosphorylated tyrosine residue at a position which corresponds to position 708 of human CSF-1R.

14. A method for detecting a complex in vitro, comprising:
  (a) providing the complex of claim 10; and
  (b) detecting said complex,
  wherein said CSF-1R comprises a phosphorylated tyrosine residue at a position which corresponds to position 699 of human CSF-1R and/or a phosphorylated tyrosine residue at a position which corresponds to position 708 of human CSF-1R.

\* \* \* \* \*